United States Patent
Ozawa et al.

(10) Patent No.: US 9,232,883 B2
(45) Date of Patent: Jan. 12, 2016

(54) ENDOSCOPE APPARATUS

(75) Inventors: Satoshi Ozawa, Kanagawa (JP);
Takayuki Iida, Kanagawa (JP);
Yasuhiro Minetoma, Kanagawa (JP);
Akihiko Erikawa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 362 days.

(21) Appl. No.: 13/017,349

(22) Filed: Jan. 31, 2011

(65) Prior Publication Data
US 2011/0237894 A1     Sep. 29, 2011

(30) Foreign Application Priority Data

Mar. 29, 2010 (JP) ................................. 2010-076457

(51) Int. Cl.
| A61B 1/06 | (2006.01) |
| A61B 1/00 | (2006.01) |
| A61B 1/04 | (2006.01) |
| A61B 1/07 | (2006.01) |

(52) U.S. Cl.
CPC ............. *A61B 1/00188* (2013.01); *A61B 1/043* (2013.01); *A61B 1/063* (2013.01); *A61B 1/0638* (2013.01); *A61B 1/0653* (2013.01); *A61B 1/0684* (2013.01); *A61B 1/07* (2013.01)

(58) Field of Classification Search
CPC .......................... A61B 1/00009; A61B 1/0638
USPC ......................................................... 362/574
See application file for complete search history.

(56) References Cited

U.S. PATENT DOCUMENTS

| 4,845,554 A | * | 7/1989 | Kimura et al. .................. 348/69 |
| 6,254,531 B1 | * | 7/2001 | Higuchi et al. ............... 600/178 |
| 6,331,156 B1 | * | 12/2001 | Haefele et al. ................ 600/179 |

(Continued)

FOREIGN PATENT DOCUMENTS

| EP | 2335551 A1 | 6/2011 |
| EP | 2 436 304 A2 | 4/2012 |

(Continued)

OTHER PUBLICATIONS

European Search Report, Jul. 20, 2011.

(Continued)

*Primary Examiner* — Anhtuan T Nguyen
*Assistant Examiner* — Jae Woo
(74) *Attorney, Agent, or Firm* — McGinn IP Law Group, PLLC (57) ABSTRACT

To provide an endoscope apparatus in which the observation image can be varied continuously as the observation magnification is varied by a zoom magnification varying manipulation so that an observation image suitable for an endoscope diagnosis is obtained at each observation magnification, and to thereby prevent the operator from feeling uncomfortable and increase the accuracy of a diagnosis. An endoscope apparatus is equipped with illuminating unit having plural light sources which generate light beams having different spectra, for illuminating an observation subject; imaging unit for imaging the observation subject; observation magnification varying unit for varying observation magnification of the imaging of the imaging unit; and light quantity ratio varying unit for continuously varying an emission light quantity ratio between the plural light sources according to the observation magnification that is set by the observation magnification varying unit.

12 Claims, 9 Drawing Sheets

(56) References Cited

U.S. PATENT DOCUMENTS

| | | | |
|---|---|---|---|
| 6,692,431 B2 * | 2/2004 | Kazakevich | 600/178 |
| 8,279,275 B2 * | 10/2012 | Gono et al. | 348/65 |
| 2004/0064018 A1 * | 4/2004 | Dunki-Jacobs et al. | 600/178 |
| 2007/0088192 A1 * | 4/2007 | Takeuchi et al. | 600/101 |
| 2009/0058999 A1 | 3/2009 | Gono et al. | |
| 2009/0167149 A1 | 7/2009 | Ito | |
| 2009/0290811 A1 * | 11/2009 | Imai | 382/285 |
| 2010/0054576 A1 * | 3/2010 | Tsujita | 382/134 |
| 2010/0097454 A1 * | 4/2010 | Kubo et al. | 348/65 |
| 2011/0032350 A1 | 2/2011 | Kikuchi et al. | |
| 2011/0184243 A1 * | 7/2011 | Wright et al. | 600/180 |
| 2011/0237894 A1 * | 9/2011 | Ozawa et al. | 600/168 |
| 2013/0267781 A1 | 10/2013 | Ito | |

FOREIGN PATENT DOCUMENTS

| | | | |
|---|---|---|---|
| JP | 3583731 A | 4/2002 | |
| JP | 2006-0341077 A | 12/2006 | |
| JP | 2007-20728 A | 2/2007 | |
| JP | 2007020728 A | 2/2007 | |
| JP | 2009-22375 A | 2/2009 | |
| JP | 2009-153712 A | 7/2009 | |
| JP | 2009-259703 A | 11/2009 | |
| JP | 2010-046354 A | 3/2010 | |
| WO | 2009128391 A1 | 10/2009 | |
| WO | WO 2009128391 A1 * | 10/2009 | G01N 21/25 |

OTHER PUBLICATIONS

European Search Report dated May 2, 2013.

Japanese Office Action dated Jul. 2, 2013 with partial English translation thereof.

Chinese Office Action dated Mar. 4, 2014 with an English Translation.

Japanese Office Action dated May 20, 2014 with partial English Translation.

* cited by examiner

ENDOSCOPE APPARATUS

The present application claims priority from Japanese Patent Application No. 2010-079457 filed on Mar. 29, 2010, the entire content of which is incorporated herein by reference.

BACKGROUND OF INVENTION

1. Field of the Invention

The present invention relates to an endoscope apparatus.

2. Description of the Related Art

Usually, a white light source is used in endoscope apparatus. However, in recent years, endoscope apparatus that enable special light observation such as narrow-band light observation in which a fine structure of a surface layer of mucosa tissue is emphasized with illumination by light in a particular narrow wavelength band (narrow-band light) and fluorescence observation in which fluorescence emitted from a fluorescent substance given in advance or living body tissue have come to be used (refer to JP-B-3,583,731, for example). By virtue of special light observation, endoscope apparatus of this kind can easily visualize living body information that cannot be obtained from an ordinary observation image. For example, they can emphasize a lesion and a fine structure of new blood vessels formed in a mucosa layer or a mucosa lower layer.

In diagnoses using an endoscope apparatus, to find a lesion, it is effective to examine a distant-view image covering a wide range that is taken by wide-angle shooting. And to observe the thus-found lesion, it is effective to examine a short-range-view image taken by enlarged shooting. White light is mainly used for the distant-view observation and narrow-band special light is used for the short-range-view observation to emphasize a fine structure or a lesion. The light source type used is switched in synchronism with an observation magnification change which is caused by a zoom magnification varying manipulation (refer to JP-A-2007-20728, for example).

However, where switching is merely made between white light and special light depending on whether short-range-view shooting or distant-view shooting is being performed, the manner of image display is not varied continuously in link with a zoom magnification varying manipulation. Instead, the illumination light is switched from white light to special light at a particular observation magnification value and the content of the observation image is changed suddenly, which is uncomfortable to the operator. Furthermore, the illumination light cannot be adjusted finely to attain optimum illumination according to the observation magnification.

SUMMARY OF INVENTION

An object of the present invention is to provide an endoscope apparatus in which the observation image can be varied continuously as the observation magnification is varied by a zoom magnification varying manipulation so that an observation image suitable for an endoscope diagnosis is obtained at each observation magnification, and to thereby prevent the operator from feeling uncomfortable and increase the accuracy of a diagnosis.

(1) According to an aspect of the invention, an endoscope apparatus includes: an illuminating unit having plural light sources which generate light beams having different spectra, which illuminates an observation subject; an imaging unit which images the observation subject; an observation magnification varying unit which varies observation magnification of the imaging of the imaging unit; and a light quantity ratio varying unit which continuously varies an emission light quantity ratio between the plural light sources according to the observation magnification that is set by the observation magnification varying unit.

In the endoscope apparatus according to the embodiment, the observation image can be varied continuously as the observation magnification is varied by a zoom magnification varying manipulation so that an observation image suitable for an endoscope diagnosis is obtained at each observation magnification, whereby the operator is prevented from feeling uncomfortable and the accuracy of a diagnosis can be increased.

DESCRIPTION OF EXEMPLARY EMBODIMENTS

An embodiment of the present invention will be hereinafter described with reference to the drawings.

Figure 1:
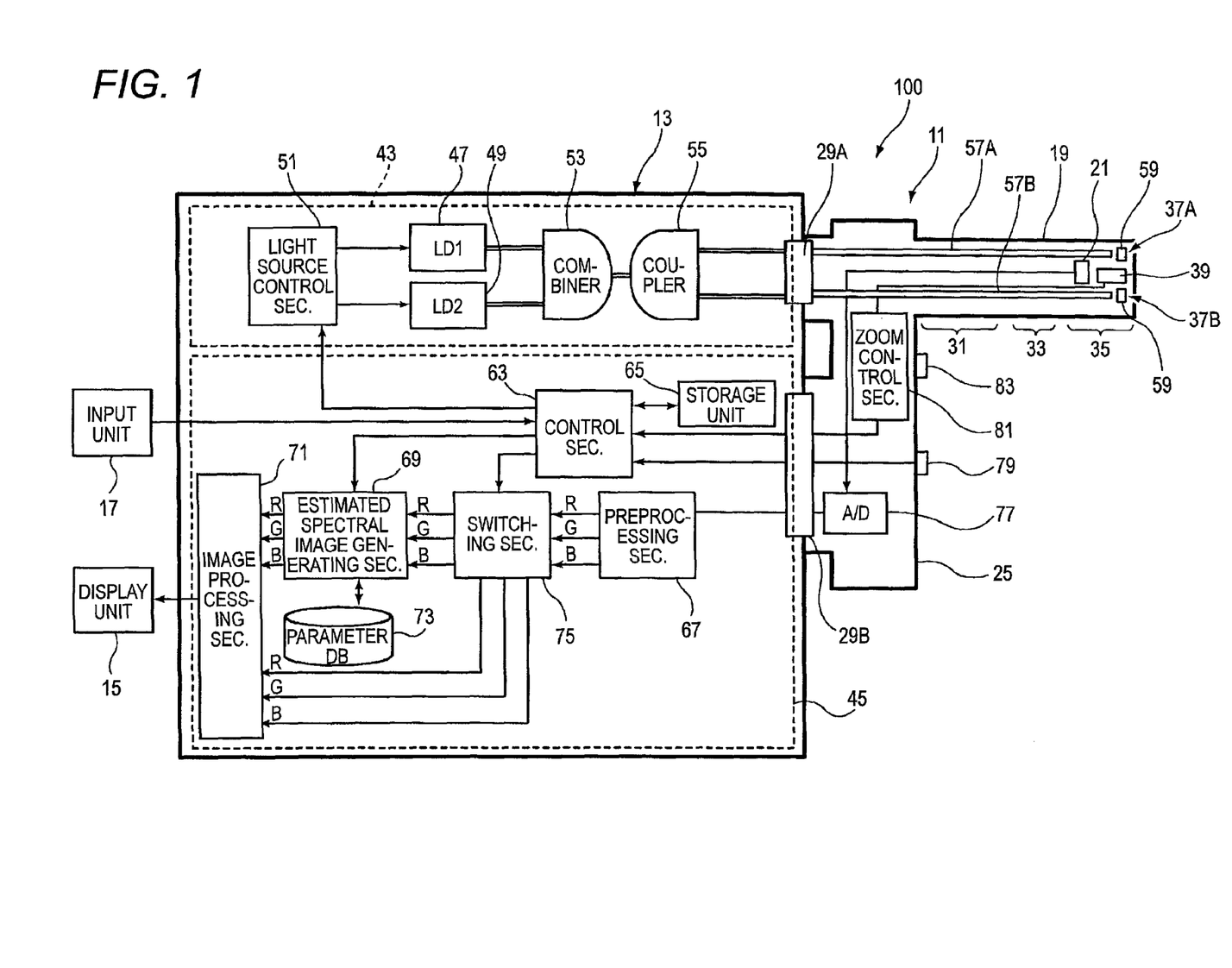
FIG. 1 is a conceptual block diagram showing the configuration of an endoscope apparatus according to an embodiment of the present invention.
Figure 2:
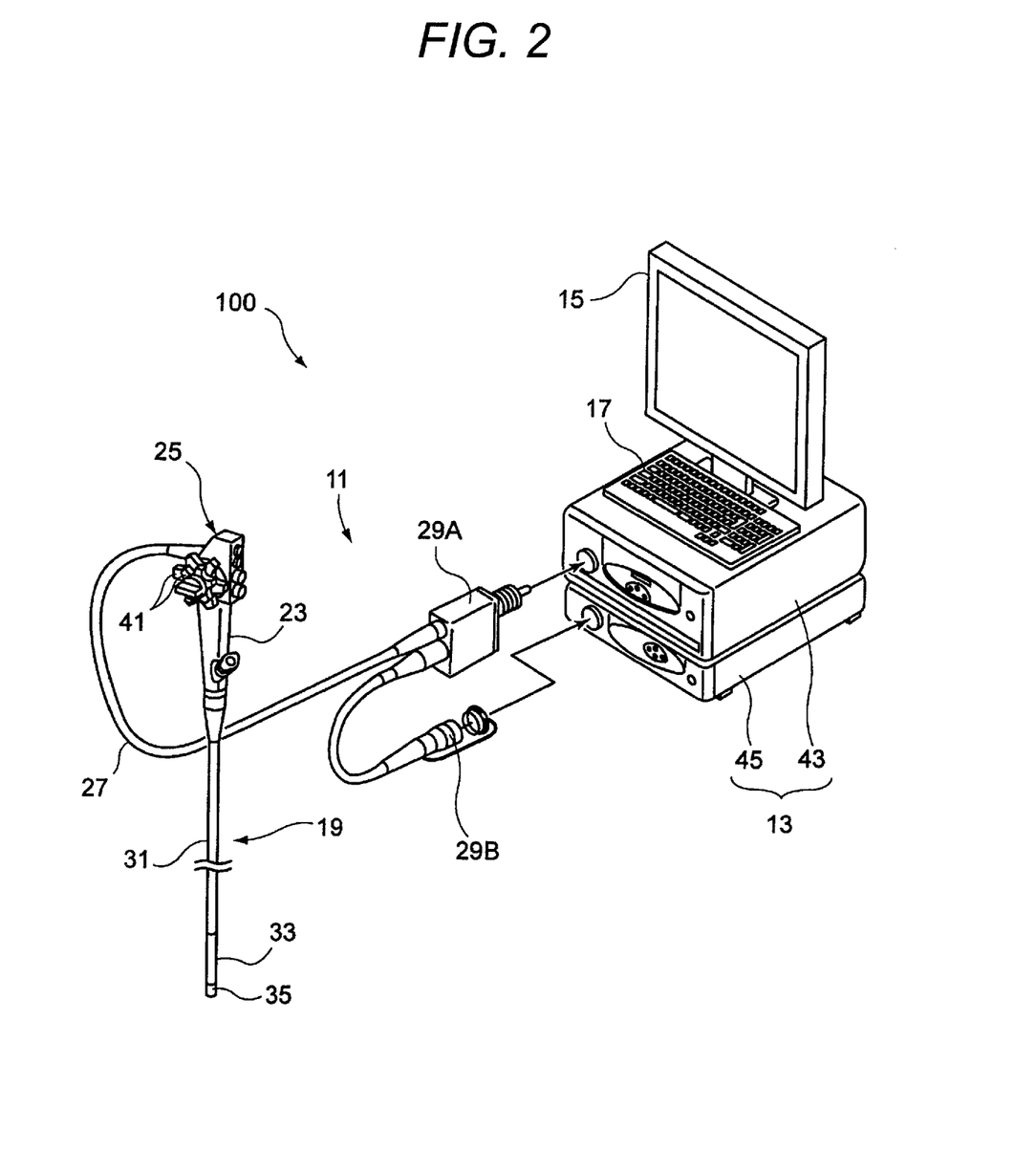
FIG. 2 shows an appearance of an example of the endoscope apparatus of FIG. 1.

FIG. 1 is a conceptual block diagram showing the configuration of an endoscope apparatus according to the embodiment of the invention. FIG. 2 shows an appearance of an example of the endoscope apparatus of FIG. 1.

As shown in FIGS. 1 and 2, the endoscope apparatus 100 is equipped with an endoscope main body 11 and a control apparatus 13 to which the endoscope main body 11 is connected. A display unit 15 for displaying image information etc. and an input unit 17 for receiving an input manipulation are connected to the control apparatus 13. The endoscope main body 11 is an electronic endoscope which has an illumination optical system for emitting illumination light from a tip portion of an endoscope insertion unit 19 and an imaging optical system including an imaging device 21 (imaging means; see FIG. 1) for imaging an observation region and an objective lens unit 39 which is a variable magnification optical system.

The endoscope main body 11 is equipped with the endoscope insertion unit 19 to be inserted into a subject body, a manipulation unit 25 (see FIG. 2) which is connected to the endoscope insertion unit 19 via an intermediate portion 23 and used for performing a manipulation for curving the tip portion of the endoscope insertion unit 19 and a manipulation for observation, and connector units 29A and 29B which connect the endoscope main body 11 to the control apparatus 13 detachably via a universal cable 27. Although not shown in FIG. 1 or 2, various channels such as a forceps channel through which to insert a tissue picking tool or the like and an air/water feed channel are formed inside the manipulation unit 25 and the endoscope insertion unit 19.

The endoscope insertion unit 19 is composed of a flexible soft portion 31, a bendable portion 33, and a tip portion (hereinafter also referred to as an endoscope tip portion) 35. As shown in FIG. 1, illumination windows 37A and 37B through which to illuminate an observation region with light and the imaging device 21 such as a CCD (charge-coupled device) image sensor or a CMOS (complementary metal-oxide-semiconductor) image sensor for acquiring image information from the observation region are arranged in the endoscope tip portion 35. The above-mentioned objective lens unit 39 is disposed adjacent to the photodetecting surface of the imaging device 21.

The bendable portion 33, which is located between the soft portion 31 and the tip portion 35, can be bent freely by a manipulation of rotating angle knobs 41 which are provided in the manipulation unit 25. The bendable portion 33 can be bent to any direction at any angle according to, for example, a part to be observed of a subject body by the endoscope main body 11, whereby the illumination/observation direction of the illumination windows 37A and 37B and the imaging device 21 provided in the endoscope tip portion 35 can be directed to a desired part to be observed. Although not shown in FIGS. 1 and 2, the illumination windows 37A and 37B of the endoscope tip portion 35 are provided with cover glasses and lenses.

The control apparatus 13 is equipped with a light source apparatus 43 (illuminating means) for generating illumination light to be supplied to the illumination windows 37A and 37B of the endoscope tip portion 35 and a processor 45 (endoscope image processing device) for performing image processing on an image signal that is supplied from the imaging device 21. The control apparatus 13 is connected to the endoscope main body 11 by the connector units 29A and 29B. The above-mentioned display unit 15 and input unit 17 are connected to the processor 45. The processor 45 performs image processing on an image signal that is transmitted from the endoscope main body 11, generates a display image, and supplies it to the display unit 15 according to an instruction that is supplied from the manipulation unit 25 of the endoscope main body 11 or the input unit 17.

The light source apparatus 43 is equipped with a blue laser light source (semiconductor light-emitting device, white illumination light source) 47 having a center wavelength 445 nm and an violet laser light source (semiconductor light-emitting device, special light source) 49 having a center wavelength 405 nm. Light emitting operations of the light sources 47 and 49 are controlled individually by a light source control section 51, whereby the light quantity ratio between light emitted from the blue laser light source 47 and light emitted from the violet laser light source 49 can be changed in a desired manner. The center emission wavelength of the special light source should be in a range of 370 to 470 nm. The lower limit value 370 nm facilitates acquisition of a semiconductor light-emitting device on the market. The upper limit value 470 nm makes it possible to produce illumination light in a wavelength range that is suitable for narrow-band light observation with emphasis on a fine structure of a surface layer of mucosa tissue.

In the embodiment, the center emission wavelength of the special light source is a wavelength (405 nm) for emphasizing a fine blood vessel structure of a living body tissue surface layer as an observation subject. That is, when it is desired to perform short-range-view observation of fine blood vessels, the special light wavelength for emphasizing a fine blood vessel structure of a living body tissue surface layer is set automatically, that is, the illumination light wavelength that is suitable for a manipulation magnification value is set automatically.

Each of the blue laser light source 47 and the violet laser light source 49 may be a broad-area-type InGaN laser diode, and may also be an InGaNAs laser diode or a GaNAs laser diode. Alternatively, each light source may be another type of light-emitting device such as a light-emitting diode.

Laser beams emitted from the light sources 47 and 49 are introduced into optical fibers through condenser lenses (not shown), respectively, and transmitted to the connector unit 29A via a combiner (multiplexer) 53 and a coupler (demultiplexer) 55. However, the invention is not limited to this structure; laser beams emitted from the light sources 47 and 49 may be sent directly to the connector unit 29A without using the combiner 53 and the coupler 55.

Figure 3:
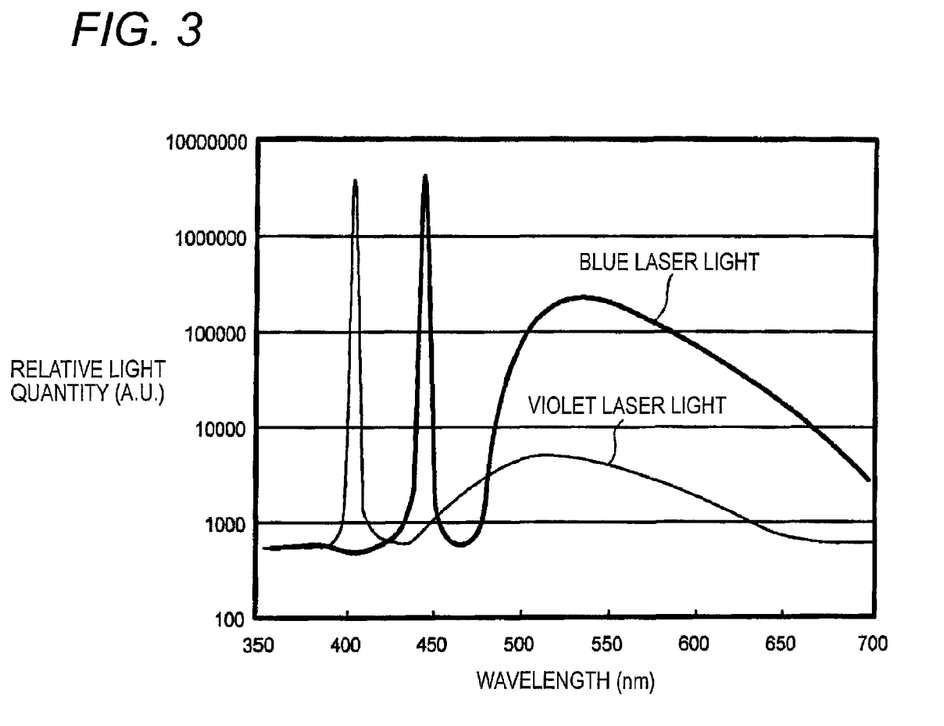
FIG. 3 is a graph showing example spectra of illuminating means.

FIG. 3 is a graph showing example spectra of the illuminating means. The blue laser light excites a phosphor 59 (wavelength conversion member) disposed at the light emission end of the optical fiber 57A of the endoscope tip portion 35 and thereby causes the phosphor 59 to emit fluorescent light. That is, the white illumination light source is formed by the semiconductor light-emitting device and the wavelength conversion member including the phosphor 59 which is excited at the emission wavelength of the semiconductor light-emitting device. Light emitted from the semiconductor light-emitting device excites the phosphor 59 to cause it to emit fluorescent light, whereby white light is obtained. Part of the blue laser light passes through the phosphor 59. On the other hand, since the excitation emission efficiency of the phosphor 59 is lower for the violet laser light which is guided by the optical fiber 57B than for the blue laser light, the proportion of violet laser light that passes through the phosphor 59 is larger than that of blue laser light. On the longer wavelength side, the violet laser light causes the phosphor 59 to emit fluorescent light having lower intensity through excitation than the blue laser light does. Violet laser light that passes through the phosphor 59 serves as narrow-wavelength-band illumination light.

With the light-source-related configuration of the embodiment, mixing illumination light of the blue laser light having the center wavelength 445 nm and illumination light of the violet laser light having the center wavelength 405 nm improves the color tone of white light because a wavelength component in a wavelength range of 460 to 470 nm that is insufficient in the illumination light of the blue laser light having the center wavelength 445 nm is compensated for by the same wavelength component of the illumination light of the violet laser light having the center wavelength 405 nm.

As such, the light source apparatus 43 has the white illumination light source and the special light source which produces illumination light that is different than the white illumination light source does. The control section 63 performs such a control as to increase the ratio of the emission light quantity of the special light source (i.e., ultraviolet laser light source 49) to that of the white illumination light source as the observation magnification increases. As a result, as the degree of short-range-view observation becomes higher, the emission light quantity of the special light source is increased and hence a narrow-band light observation image obtained with illumination by the narrow-band light having the particular wavelength is emphasized more.

Each of the optical fibers 57A and 57B is a multimode fiber and may be, for example, a small-diameter fiber cable in which the core diameter is 105 μm, the clad diameter is 125 μm, and the diameter of the cable including a protective layer (outer sheath) is 0.3 to 0.5 mm.

Each phosphor 59 contains plural kinds of phosphor substances (e.g., YAG phosphor or BAM ($BaMgAl_{10}O_{17}$)) that are excited when absorbing part of blue laser light and emit green to yellow light. White (quasi-white) illumination light is generated as a combination of green to yellow light emitted through excitation by part of blue laser light and the other part of the blue laser light that passes through the phosphor 59 without being absorbed. In the embodiment, since the semiconductor light-emitting devices are used as the excitation light sources, high-intensity white light can be obtained with high emission efficiency, the intensity of white light can be adjusted easily, and variations in color temperature and chromaticity of white light can be made small.

The phosphors 59 can prevent superimposition of imaging-obstructive noise or occurrence of a flicker at the time of display of a moving image which would otherwise be cause by a speckle pattern that is produced due to the coherence of laser light. It is preferable that the phosphor substances constituting the phosphors 59 and a fixing/solidifying resin (filler) have such particle diameters as to be low in absorption and high in scattering for infrared light taking their differences in refractive index into consideration. This enhances the scattering effect and lowers the optical loss without decrease in light intensity for red light or infrared light. That is, high-intensity white light can be obtained with high efficiency.

Figure 4:
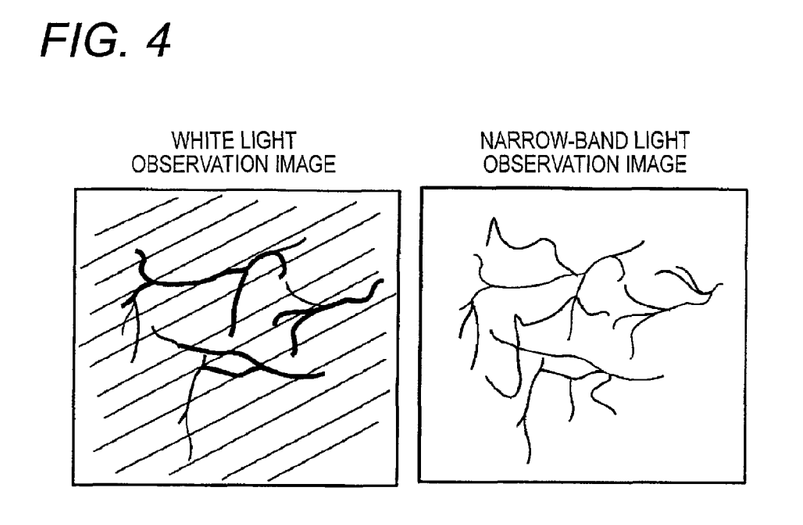
FIG. 4 schematically shows example observation images displayed by the endoscope apparatus.

FIG. 4 schematically shows example observation images displayed by the endoscope apparatus 100.

When illumination light enters living body tissue, the incident light travels through the living body tissue diffusely. The absorption/scattering characteristics of living body tissue depend on the wavelength; that is, the scattering becomes stronger as the wavelength becomes shorter. Therefore, the depth reached by illumination light depends on its wavelength. On the other hand, blood flowing through a blood vessel has an absorption peak in a wavelength range of 400 to 420 nm and high contract is obtained in that wavelength range. For example, blood vessel information of capillary vessels of a mucosa surface layer is obtained by illumination light in a wavelength range around 400 nm, and blood vessel information of blood vessels including ones located in a deeper layer is obtained by illumination light in a wavelength range around 500 nm. Therefore, for observation of blood vessels in a surface layer of living body tissue, a light source having a center wavelength 360 to 800 nm, preferably 365 to 515 nm and even preferably 400 to 470 nm, is used.

As shown in FIG. 4, in an observation image obtained using white illumination light, whereas images of blood vessels located in a relatively deep mucosa layer can be obtained, fine capillary vessels in a mucosa surface layer are blurred. On the other hand, in an observation image obtained using narrow-band illumination light having only a short wavelength, fine capillary vessels in the mucosa surface layer can be seen clearly.

In the endoscope apparatus 100, the light quantity ratio between the blue laser light source 47 and the violet laser light source is variable. The light quantity ratio is varied by the control section 63 shown in FIG. 1 and blood vessels in a mucosa surface layer are emphasized in an image to facilitate their observation. Where the blue laser light component of the blue laser light source 47 is dominant, illumination light is produced in which a white light component as a combination of blue laser light and light emitted from the phosphor 59 through excitation is dominant and an observation image like the white light observation image shown in FIG. 4 is obtained. However, since the blue laser light is mixed in the illumination light, capillary blood vessels in a surface layer is emphasized in the observation image.

Where the violet laser light component of the violet laser light source 49 is dominant, an observation image like the narrow-band light observation image shown in FIG. 4 is obtained. Fine capillary vessels in a mucosa surface layer can be observed in such a manner as to continue to be displayed in an emphasized manner by varying the light quantity ratio between the light beams emitted from the blue laser light source 47 and the violet laser light source (i.e., varying the proportion of the violet laser light component in the entire illumination light).

As the proportion of the violet laser light component increases, fine capillary vessels in a mucosa surface layer which is thin in the depth direction are shown more clearly in an observation image. As the proportion of the violet laser light component decreases, information of blood vessels located in a thicker region from the mucosa surface layer to its deep layer are shown. In this manner, a blood vessel distribution in the depth direction from the mucosa surface layer can be displayed in an emphasized manner and the blood vessel information of an observation part can be extracted as continuous pieces of information corresponding to respective depth ranges. In particular, in the embodiment, since blood vessel information extracted by blue laser light and blood vessel information of a surface layer extracted by violet laser light can be compared with each other through image display, information of blood vessels including the ones located in the surface layer can be observed with increased legibility.

Incidentally, the objective lens unit 39 of the endoscope apparatus 100 is provided with a magnification-varying movable lens (not shown). The magnification-varying movable lens is incorporated in the objective lens unit 39 in a movable manner and thereby serves to vary the observation magnification. The objective lens unit 39 is also provided, separately from the magnification-varying movable lens, with a focus-adjusting movable lens (not shown) for performing an auto-focus function. The magnification-varying movable lens is driven via a zoom control section 81 (observation magnification varying means) according to a manipulation on a zoom switch 83.

The endoscope apparatus 100 is provided with a light quantity varying means for varying the light quantity ratio between light beams emitted from the plural light sources according to an observation magnification value that is set by the zoom control section 81. For example, the light quantity varying means is a program stored in a storage unit 65. The light quantity varying means the light quantity ratio between the blue laser light source 47 and the violet laser light source 49 by referring to a magnification detection signal that is supplied from the zoom control section 81. A resulting light quantity ratio control signal is supplied to the light source control section 51.

The observation magnification value may be an enlargement value of digital zoom processing. In this case, an enlargement value of image processing for enlarging shot image information is used as an observation magnification value.

Figure 5:
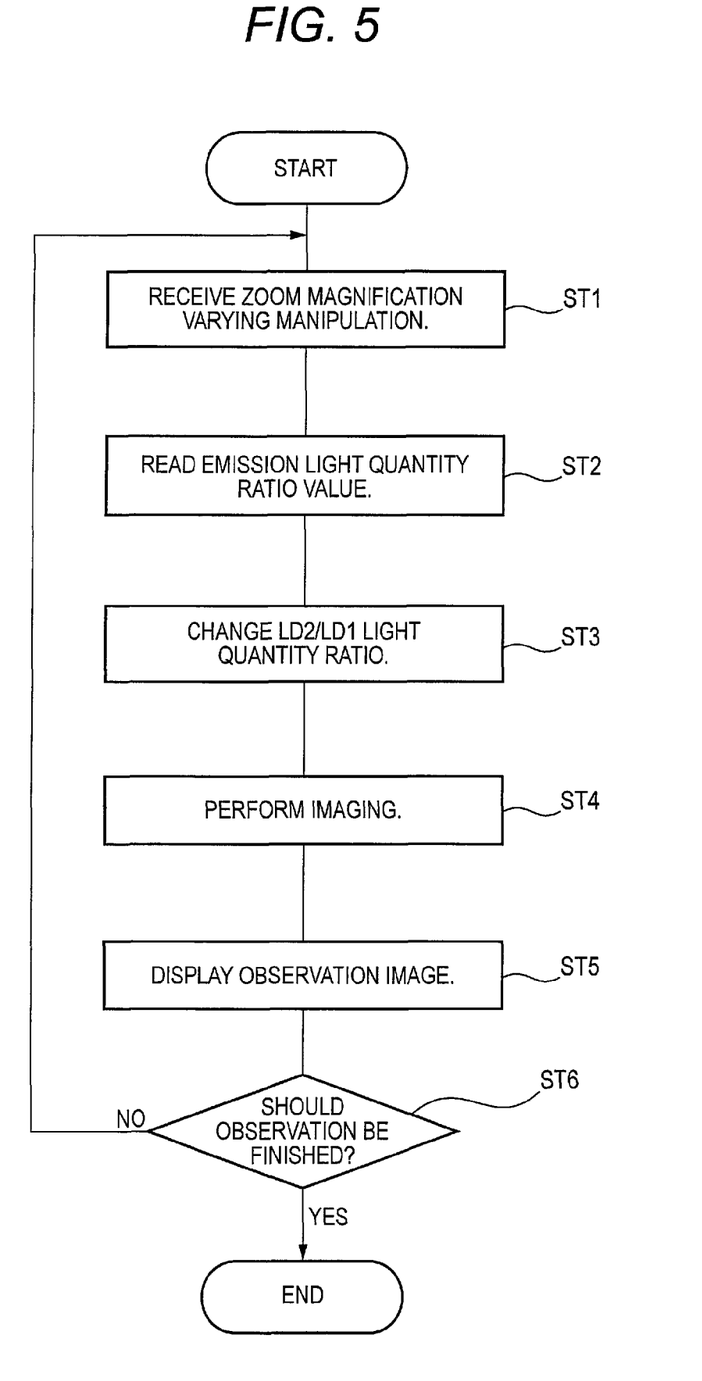
FIG. 5 is a flowchart of a procedure of varying the emission light quantity ratio according to the observation magnification.

FIG. 5 is a flowchart of a procedure of varying the emission light quantity ratio according to the observation magnification.

As the operator varies the observation magnification in a direction from distant-view observation to short-range-view observation or vice versa by a zoom magnification varying manipulation (ST1), each resulting magnification detection signal is detected by the zoom control section 81 and input to a light quantity ratio varying means. At step ST2, every time the light quantity ratio varying means receives a magnification detection signal, the light quantity ratio varying means reads a corresponding emission light quantity ratio between the blue laser light source 47 and the violet laser light source 49 from light quantity ratio-observation magnification conversion information stored in the storage unit 65 and performs updating.

The following Table 1 shows example light quantity ratio-observation magnification conversion information. The ratio of the light quantity of the violet laser light source 49 to that of the blue laser light source 47 is set at 2:1, for example, in a distant-view observation mode in which the observation magnification is low, and at 10:1, for example, in a short-range-view observation mode in which the observation magnification is high.

TABLE 1

| Observation magnification | Mode | Light quantity ratio R LD2 (405 nm):LD1 (445 nm) |
|---|---|---|
| Low | Distant-view observation | 2:1 |
| High | Short-range-view observation | 10:1 |

Figure 6:
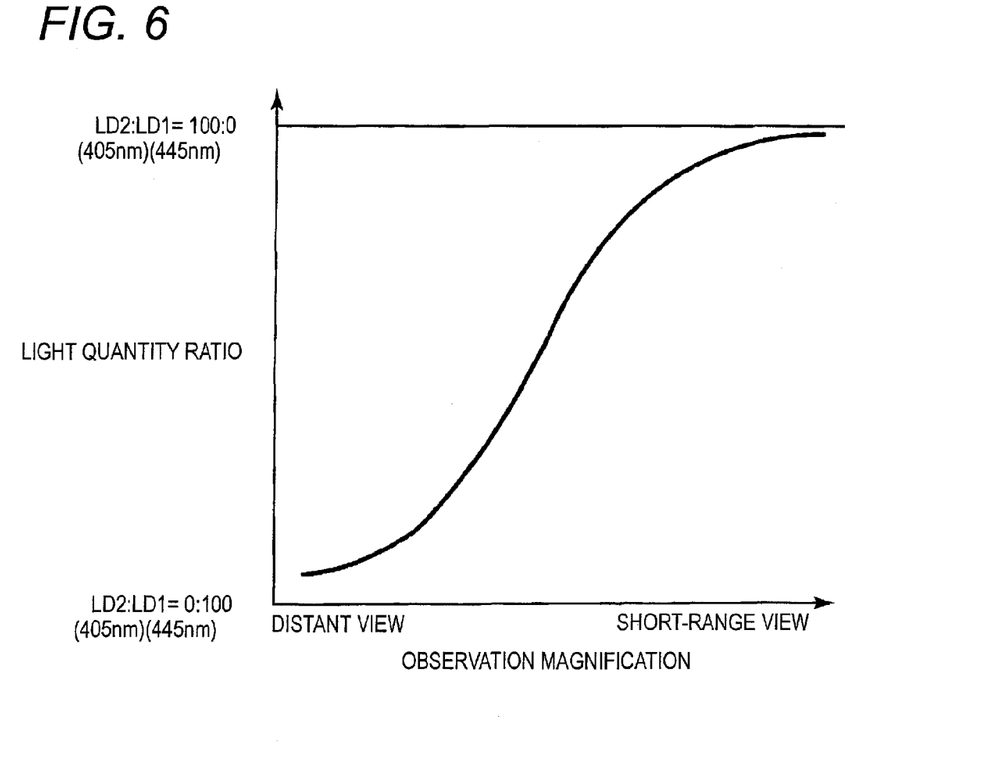
FIG. 6 is a graph showing a relationship between the observation magnification and the light quantity ratio.

FIG. 6 is a graph showing a relationship between the observation magnification and the light quantity ratio. The proportion of the light quantity of the blue laser light source 47 is increased as the degree of distant-view observation increases (i.e., the observation magnification decreases), and the proportion of the light quantity of the violet laser light source 49 is increased as the degree of short-range-view observation increases (i.e., the observation magnification increases). For example, the light quantity ratio-observation magnification conversion information is stored as a preset function equation. That is, a function representing the curve shown in FIG. 6 is determined in advance. In this case, emission light quantity ratio values can be determined continuously for arbitrary observation magnification values.

Upon reading of the emission light quantity ratio, at step ST3 the light quantity ratio varying means supplies the light control section 51 with a control signal for changing the light quantity ratio between the blue laser light source 47 and the violet laser light source 49. Imaging is performed at step ST4. An endoscope observation image signal that is output from the imaging device 21 is converted by an A/D converter 77 shown in FIG. 1 into a digital signal, which is supplied to secondary circuits headed by a preprocessing section 67. The preprocessing section 67 is to perform preprocessing on an endoscope observation image signal and has a function of converting the digital endoscope observation image signal into a signal of the RGB primary color system if the former is of the CMY or CMYG complementary color system, a gamma conversion function, a gradation adjusting function, and other functions. The endoscope observation image signal as processed by the preprocessing section 67 is supplied to the image processing section 71 and displayed on the display unit 15 at step ST5. At step ST6, the display on the display unit 15 is finished upon input of an observation end signal.

As described above, in the endoscope apparatus 100, the light quantity ratio between light beams emitted from the plural light sources is varied continuously by the light quantity ratio varying means as the observation magnification is varied. This prevents a sudden change in the content of an observation image.

Figure 7:
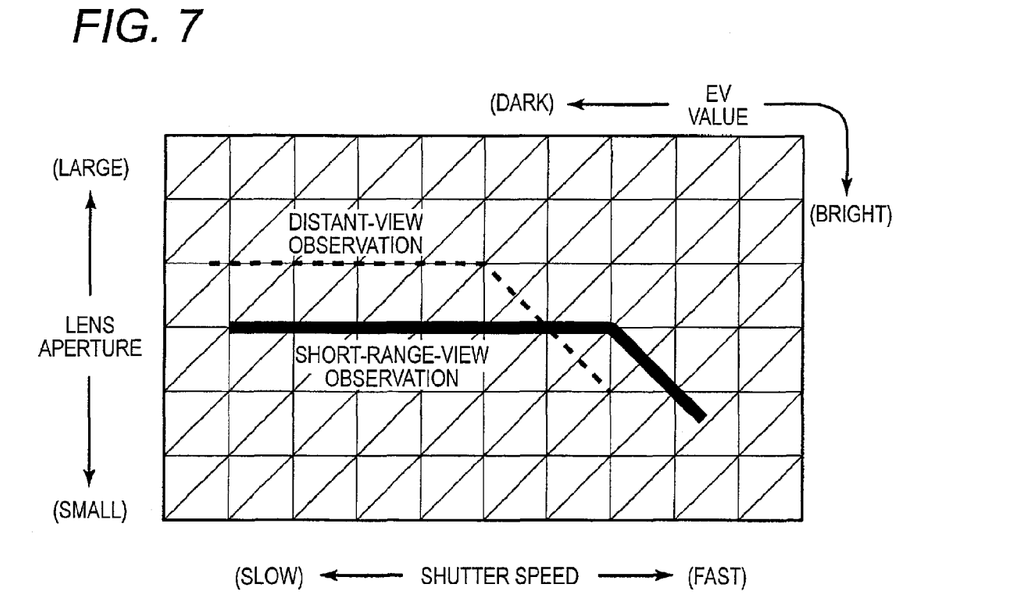
FIG. 7 shows an AE program diagram having the observation magnification as a parameter.

FIG. 7 shows an AE program diagram having the observation magnification as a parameter. The control section 63 automatically sets the shutter speed, the aperture, etc. according to the observation magnification using the AE program diagram, and thereby compensates for a camera shake in an enlarged observation. As shown in FIG. 7, each exposure value (EV value) is represented by a bottom-left-to-top-right diagonal equivalent line. The horizontal axis represents the shutter speed and the vertical axis represents the aperture. In FIG. 7, the broken-line curve corresponds to distant-view observation and the solid-line curve corresponds to short-range-view observation (enlarged observation). When a subject is bright, correct exposure is obtained by evenly adjusting the aperture and the shutter speed. When a subject is sufficiently bright, the lens aperture is set at a minimum value and the exposure is adjusted by the shutter speed. In enlarged observation, a signal indicating a position of the magnification-varying movable lens is supplied from the zoon control section 81 (see FIG. 1) to the control section 63, and the control section 63 adjusts the shutter speed according to a curve corresponding to an observation magnification value employed. The curve for enlarged observation is shifted rightward from that for distant-view observation. As a result, in enlarged observation in which the observation magnification is large, the curve with faster shutter speeds is used and hence a control is performed so as to make influence of a camera shake less conspicuous.

The endoscope apparatus 100 has a function of properly displaying, according to an observation magnification value, in the form of an estimated spectral image, living body information that cannot be obtained from ordinary observation images; for example, the endoscope apparatus 100 can emphasize a lesion and a fine structure of new blood vessels formed in a mucosa layer or a mucosa lower layer.

Color imbalance occurs when the emission light quantity ratio is varied in the above-described manner. Therefore, it is preferable to maintain the color tone of the entire observation image by varying the degrees of spectral corrections for the respective colors according to a variation in emission light quantity ratio. The endoscope apparatus 100 can provide optimum image information for an observation subject in synchronism with a variation in observation magnification by performing proper image processing such as emphasis processing according to the observation magnification.

To process an endoscope observation image acquired by the endoscope main body 11, the processor 45 of the endoscope apparatus 100 is equipped with an estimated spectral image generating section 69 (estimated spectral image generating means), a parameter database 73, and a switching section 75.

A procedure of generating an estimated spectral image in the endoscope apparatus 100 will be described below.

A signal of an endoscope observation image that is output from the imaging device 21 is converted by the A/D converter 77 into a digital signal, which is captured by the processor 45 and input to the control section 63.

If the operator wants to view an estimated spectral image rather than an ordinary image, the operator gives an instruction by manipulating a wavelength set switching button 79 or the like of the manipulation unit 25 of the endoscope main body 11. If observation using an estimated spectral image is commanded, the endoscope observation image signal as subjected to the preprocessing in the preprocessing section 67 is supplied to the estimated spectral image generating section 69, where it is subjected to spectral estimation processing.

The estimated spectral image generating section 69 generates an estimated spectral image SP by performing a matrix operation involving matrix parameters M on the endoscope observation image P. The details of an example operation of the estimated spectral image generating section 69 are described in JP-A-2003-93336.

More specifically, the estimated spectral image generating section 69 generates an estimated spectral image SP by performing a matrix operation involving matrix parameters M according to the following Equation (1).

[Formula 1]

$$\begin{pmatrix} SP_r \\ SP_g \\ SP_b \end{pmatrix} = \begin{pmatrix} M_{00} & M_{01} & M_{02} \\ M_{10} & M_{11} & M_{12} \\ M_{20} & M_{21} & M_{22} \end{pmatrix} \begin{pmatrix} P_r \\ P_g \\ P_b \end{pmatrix} \quad (1)$$

In Equation (1), $SP_r$, $SP_g$, and $SP_b$ are the R, G, and B components of the estimated spectral image SP, $P_r$, $P_g$, and $P_b$ are the R, G, and B components of the endoscope observation image P, and $M_{00}$-$M_{22}$ are the matrix parameters $M_{ij}$ of the 3×3 matrix for the matrix operation.

Figure 8:
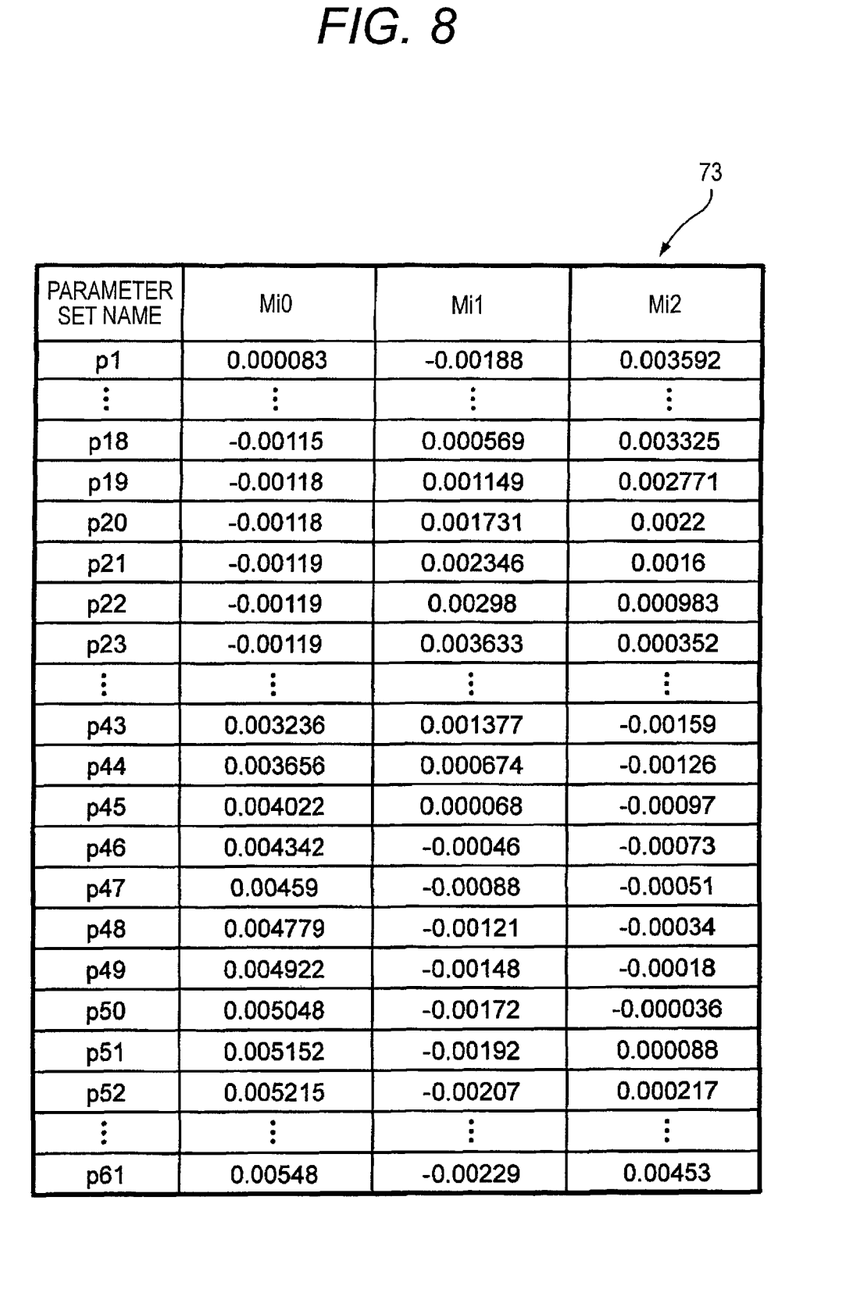
FIG. 8 is a table showing example sets of matrix parameters that are stored in a parameter database of a processor shown in FIG. 1.

FIG. 8 is a table showing example sets of matrix parameters that are stored in the parameter database 73 of the processor 45.

As shown in FIG. 8, matrix parameter sets $p_n=(M_{i0}, M_{i1}, M_{i2})$ (n=1 to 61, i (=0, 1, or 2) represents a row of the matrix of the matrix parameters M) for respective wavelength ranges that, for example, cover a wavelength range 400 to 700 nm and are separated from each other by 5 nm are stored in the parameter database 73. For example, if 500 nm, 620 nm, and 650 nm are selected as a set of wavelengths λ1, λ2, and λ3 for the estimated spectral image SP, matrix parameters M in the following Equation (2) which consist of matrix parameters (coefficients) p21 for the center wavelength 500 nm, matrix parameters (coefficients) p45 for the center wavelength 620 nm, and matrix parameters (coefficients) p51 for the center wavelength 650 nm among the 61 sets of matrix parameters shown in FIG. 8 are used as the matrix parameters ($M_{00}$, $M_{01}$, $M_{02}$), ($M_{10}$, $M_{11}$, $M_{12}$), and ($M_{20}$, $M_{21}$, $M_{22}$), respectively.

[Formula 2]

$$\begin{pmatrix} M_{00} & M_{01} & M_{02} \\ M_{10} & M_{11} & M_{12} \\ M_{20} & M_{21} & M_{22} \end{pmatrix} = \begin{pmatrix} -0.00119 & 0.002346 & 0.0016 \\ 0.004022 & 0.000068 & -0.00097 \\ 0.005152 & -0.00192 & 0.000088 \end{pmatrix} \quad (2)$$

Sets of parameters are stored in the parameter database 73 for respective parts to be observed such as blood vessels and living body tissue, and an estimated spectral image SP is generated using sets of parameters suitable for a target part. Table 2 shows example wavelength sets each for setting matrix parameters M.

TABLE 2

| No. | Type | λ1, λ2, λ3 (nm) |
|---|---|---|
| CH1 | Standard set | 400, 500, 600 |
| CH2 | Blood vessel set | 470, 500, 670 |
| CH3 | Blood vessel set | 475, 510, 685 |
| CH5 | Set for imaging of particular tissue | 440, 480, 520 |
| CH6 | Set for imaging of particular tissue | 480, 510, 580 |
| CH7 | Hemoglobin set for discrimination between oxyhemoglobin and deoxyhemoglobin | 400, 430, 475 |
| CH8 | Blood-carotene set for discrimination between blood and carotene | 415, 450, 500 |
| CH9 | Blood-cytoplasm set for discrimination between blood and cytoplasm | 420, 550, 600 |

The estimated spectral image generating section 69 performs a matrix operation on a shot image that is taken by illuminating an observation subject with white illumination light and thereby generates an estimated spectral image that would be obtained when the observation subject were illuminated with light having a spectrum that is obtained by a wavelength set that is set by the wavelength set setting means. The control section 63 stores the wavelength set setting means for doing such a matrix change. For example, the wavelength set setting means is a program stored in the storage unit 65.

The endoscope apparatus 100 may have a function of adjusting the gains of R, G, and B components using correction values that accord with sensitivity characteristics of the imaging device 21 of an individual product of the endoscope main body 11. More specifically, the estimated spectral image generating section 69 generates an estimated spectral image SP using, instead of the matrix parameters M of Equation (1), matrix parameters M1 obtained by multiplexing the matrix of the matrix parameters M by the matrix including R, G, and B gain coefficients $R_g$, $G_g$, and $B_g$ according to the following Equation (3).

[Formula 3]

$$M1 = \begin{pmatrix} R_g & 0 & 0 \\ 0 & G_g & 0 \\ 0 & 0 & B_g \end{pmatrix} \begin{pmatrix} M_{00} & M_{01} & M_{02} \\ M_{10} & M_{11} & M_{12} \\ M_{20} & M_{21} & M_{22} \end{pmatrix} \quad (3)$$

The gain coefficients $R_g$, $G_g$, and $B_g$ are changed according to the sensitivity characteristics of the imaging device 21 which are stored in, for example, a product identification memory (not shown) provided in the endoscope main body 11 used. With this measure, in the case where the estimated spectral image generating section 69 generates an estimated spectral image using a wavelength set, R, G, and B component values suitable for brightness can be obtained and hence the image quality of an estimated spectral image is enhanced.

Figure 9:
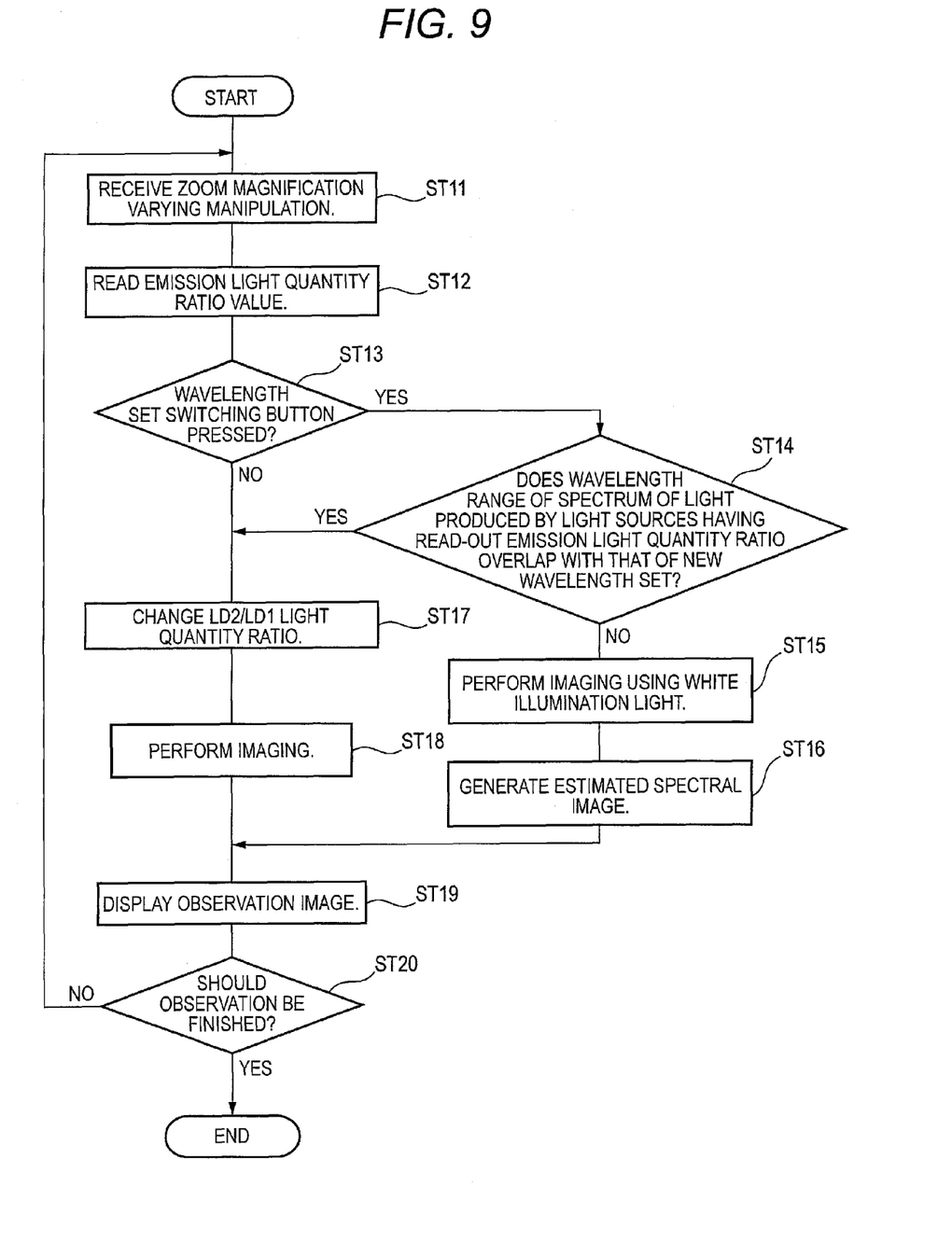
FIG. 9 is a flowchart of a procedure of varying the emission light quantity ratio according to the observation magnification in an observation with generation of an estimated spectral image.

FIG. 9 is a flowchart of a procedure of varying the emission light quantity ratio according to the observation magnification in an observation with generation of an estimated spectral image.

Provided with the wavelength set setting means and the estimated spectral image generating section 69, the endoscope apparatus 100 can generate an estimated spectral image corresponding to a desired wavelength set and use it as an observation image. A procedure of generating an estimated spectral image in the endoscope apparatus 100 will be described below.

When the zoom magnification is changed at step ST11 in the case where an observation image is to be obtained using a desired wavelength set that is set by the wavelength set setting means, an emission light quantity ratio value is read out at step ST12. At step ST13, it is judged whether or not the wavelength set switching button has been pressed. If the wavelength set switching button has been pressed, it is judged at step ST14 whether not the wavelength range of a spectrum of light produced by the blue laser light source 47 and the violet laser light source 49 having the read-out emission light quantity ratio overlaps with that of a new wavelength set.

If overlap is not found, imaging is performed using white illumination light at step ST15 and an estimated spectral image is generated at step ST16. On the other hand, overlap is found at step ST14, the emission light quantity ratio between the blue laser light source 47 and the violet laser light source 49 is changed at step ST17, imaging is performed at step ST18, and an observation image is displayed at step ST19. The above steps are executed repeatedly until it is judged at step ST20 that the observation should be finished. The display of the observation image is finished upon input of an observation end instruction.

As described above, in the endoscope apparatus 100, if the wavelength range of a spectrum determined by the read-out emission light quantity ratio between the blue laser light source 47 and the violet laser light source 49 overlaps with that of a new wavelength set, an observation image is taken using illumination light corresponding to the read-out emission light quantity ratio. If overlap is not found, the control section 63 causes the white illumination light source to emit white light and the estimated spectral image generating section 69 generates an estimated spectral image corresponding to a desired wavelength set, which is employed as an observation image. As a result, even if the ratio of the light quantity of the special light source (405 nm) to that of the white illumination light source (445 nm) is set at 100:0, an observation image which includes a white light component can be generated through spectral estimation.

An estimated spectral image may be generated from an image taken by lighting both of the white illumination light source and the special light source. This makes it possible to increase the amount of information of an estimated spectral image by necessarily leaving a wavelength component of the special light source (405 nm).

Next, modifications of the embodiment will be described. The illuminating means is not limited to the above one and may be configured as described below.

Figure 10:
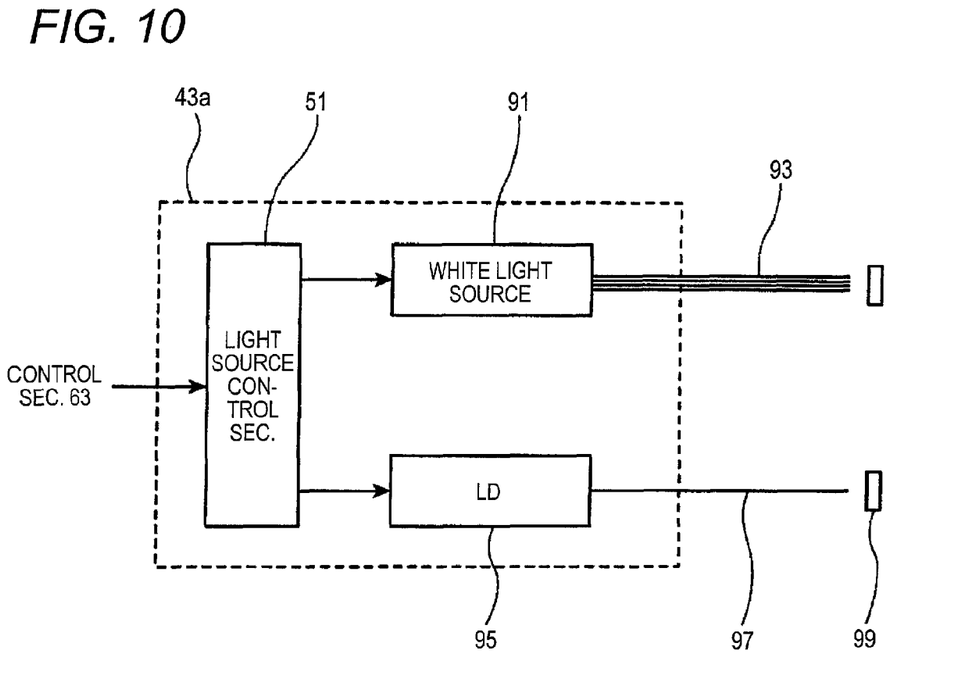
FIG. 10 is a block diagram showing the configuration of a modified light source apparatus which is equipped with a white light source and a laser light source.

FIG. 10 is a block diagram showing the configuration of a modified light source apparatus having a white light source and a laser light source. The modified light source apparatus 43a is equipped with an illumination system for outputting light that is emitted from a white light source 91 and transmitted by a fiber bundle 93 consisting of many optical fibers and an illumination system for outputting light that is emitted from a laser light source 95, is guided by a single optical fiber 97, and passes through a diffusion plate 99.

Figure 11:
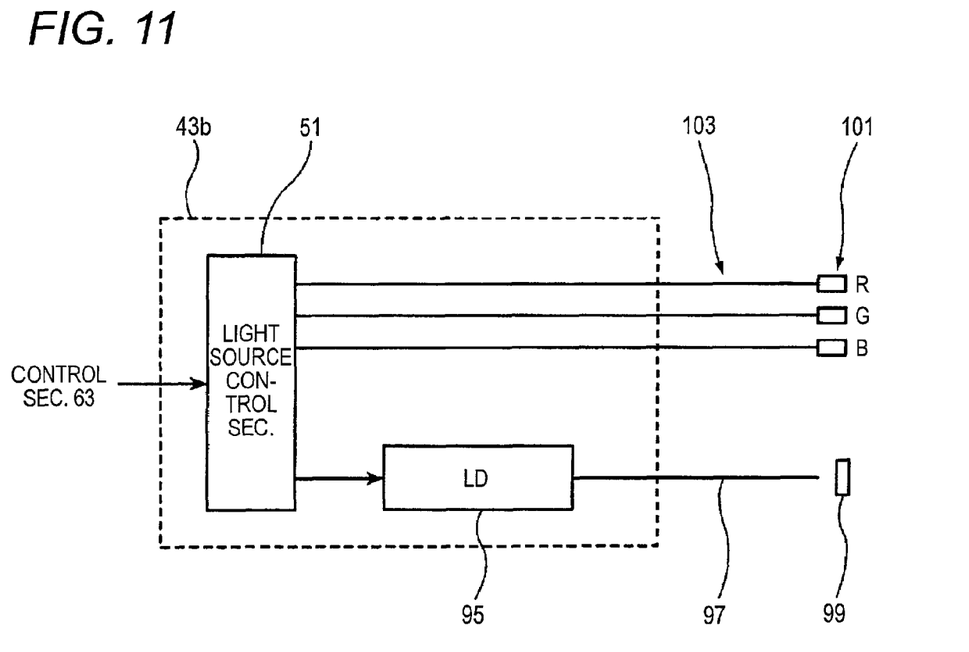
FIG. 11 is a block diagram showing the configuration of a modified light source apparatus which is equipped with LEDs and a laser light source.

FIG. 11 is a block diagram showing the configuration of a modified light source apparatus having LEDs and a laser light source. The modified light source apparatus 43b is equipped with an optical system in which R, G, and B LEDs (light-emitting diodes) 101 disposed in the tip portion 35 of the endoscope insertion unit 19 are connected to the light source control section 51 by signal lines 103 and an illumination system for outputting light that is emitted from a laser light source 95, is guided by a single optical fiber 97, and passes through a diffusion plate 99. This configuration makes it easier to give a desired wavelength range and desired intensity to each of white illumination light and narrow-band light.

Figure 12:
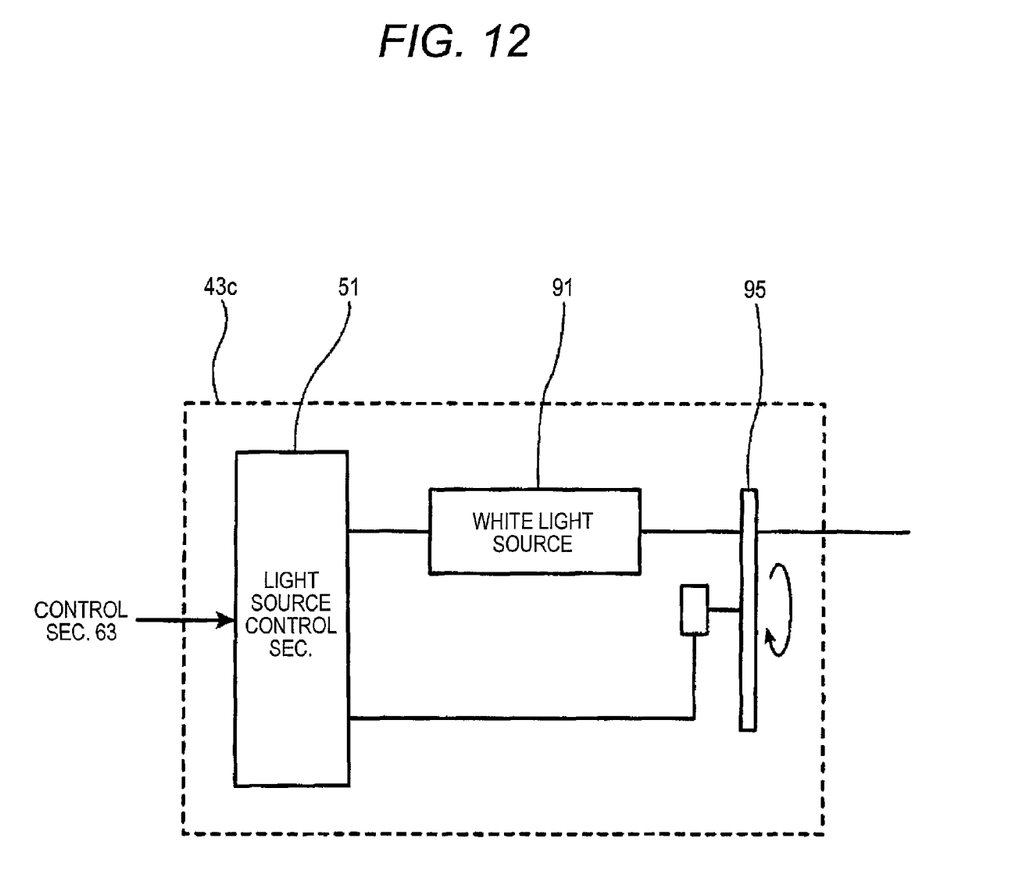
FIG. 12 is a block diagram showing the configuration of a modified light source apparatus which is equipped with a white light source and a rotary filter device.

FIG. 12 is a block diagram showing the configuration of a modified light source apparatus having a white light source and a rotary filter device. In the light source apparatus 43c, R, G, and B light beams, narrow-band light, C, M, and Y light beams, or C, M, Y, and G light beams are extracted from light emitted from a white light source 91 by using a rotary filter device 105.

The imaging device 21 may be either a CCD image sensor or a CMOS image sensor. And the imaging device 21 is not limited to the one which detects R, G, and B light beams and may be one which detects C, M, and Y light beams or C, M, Y, and G light beams.

The imaging method may be either of a simultaneous imaging type in which R, G, and B images are taken simultaneously or of a frame-sequential type in which R, G, and B images are taken sequentially and combined (by time equalization processing) later into a single color image.

In the endoscope apparatus 100, the observation image can be varied continuously as the observation magnification is varied by a zoom magnification varying manipulation so that an observation image suitable for an endoscope diagnosis is obtained at each observation magnification, whereby the operator can be prevented from feeling uncomfortable and the accuracy of a diagnosis can be increased.

As exemplified above, the invention is not limited to the above embodiment, and modifications and applications that would be made by a person skilled in the art on the basis of the disclosure of this specification and known techniques are included in the range of protection of the invention.

This specification discloses the following items:

(1) According to an aspect of the invention, an endoscope apparatus includes:
an illuminating unit having plural light sources which generate light beams having different spectra, which illuminates an observation subject;
an imaging unit which images the observation subject;
an observation magnification varying unit which varies observation magnification of the imaging of the imaging unit; and
a light quantity ratio varying unit which continuously varies an emission light quantity ratio between the plural light sources according to the observation magnification that is set by the observation magnification varying unit.

In this endoscope apparatus, as the operator varies the observation magnification in a direction from distant-view observation to short-range-view observation or vice versa by a zoom magnification varying manipulation, each resulting observation magnification value is detected by the observation magnification varying means and input to the light quantity ratio varying means. Every time the light quantity ratio varying means receives a magnification value, the light quantity ratio varying means updates the emission light quantity ratio between the plural light sources. That is, the emission light quantity ratio between the plural light sources is adjusted continuously in link with the varying magnification, whereby a sudden change in the content of an observation image can be prevented.

(2) In the endoscope apparatus of (1), the illuminating unit comprises a white illumination light source and a special light source for generating different illumination light than the white illumination light source; and
the light quantity ratio varying unit increases a ratio of an emission light quantity of the special light source to an emission light quantity of the white illumination light source as the observation magnification increases.

In this endoscope apparatus, as the observation magnification increases, that is, as the degree of short-range-view observation increases, the proportion of the emission light quantity of the special light source is increased, whereby a narrow-band light observation image that is obtained with illumination by narrow-band light having a particular wavelength is emphasized more.

(3) In the endoscope apparatus of (2), the special light source has such a center wavelength that a fine blood vessel structure in a surface layer of living body tissue as the observation subject is emphasized.

In this endoscope apparatus, when it is desired to observe fine blood vessels by a short-range observation, the special light wavelength for emphasizing a fine blood vessel structure in a surface layer of living body tissue is set. The illumination light wavelength suitable for a manipulation-instructed magnification value is thus set automatically.

(4) In the endoscope apparatus of (2), the special light source has a center wavelength that is in a range of 370 nm to 470 nm.

According to this endoscope apparatus, the lower limit value 370 nm of the center emission wavelength facilitates acquisition of a semiconductor light-emitting device on the market. The upper limit value 470 nm of the center emission wavelength makes it possible to produce illumination light in a wavelength range that is suitable for narrow-band light observation with emphasis on a fine structure of a surface layer of mucosa tissue.

(5) In the endoscope apparatus of (2), the white illumination light source comprises a semiconductor light-emitting device and a wavelength conversion member including a phosphor which is excited at an emission wavelength of the semiconductor light-emitting device.

In this endoscope apparatus, light emitted from the semiconductor light-emitting device excites the phosphor of the wavelength conversion member and causes it to emit fluorescent light and white light is thereby obtained. Part of the light emitted from the semiconductor light-emitting device passes through the wavelength conversion member without being absorbed and becomes narrow-wavelength-band illumination light.

(6) In the endoscope apparatus of (2), the white illumination light source comprises semiconductor light-emitting devices for emitting red light, green light, and blue light, respectively.

In this endoscope apparatus, white illumination light is obtained by driving red, green, and blue LEDs (light-emitting diodes) which are provided in the tip portion of the endoscope insertion unit. Narrow-wavelength-band illumination light may be obtained by guiding light emitted from a laser light source by a single optical fiber. This configuration makes it easier to give a desired wavelength range and desired intensity to each of white illumination light and narrow-band light.

(7) In the endoscope apparatus of (1), the observation magnification is magnification of a variable magnification optical system.

In this endoscope apparatus, a moving focal point position of a magnification-varying movable lens is detected by a sensor and a resulting detection signal is used as a signal indicating an observation magnification value.

(8) In the endoscope apparatus of (1), the observation magnification is magnification of digital zoom processing.

In this endoscope apparatus, an enlargement value of image processing for enlargement of shot image information is used as an observation magnification value.

(9) The endoscope apparatus of (2), further comprising:
a wavelength set setting unit which sets a wavelength set which is a combination of plural wavelength ranges; and
an estimated spectral image generating unit which generates an estimated spectral image which would be obtained when the observation subject is illuminated with light having a spectrum that is produced by the wavelength set that is set by the wavelength set setting unit by performing a matrix operation on an observation image taken by illuminating the observation subject with white illumination light, wherein:
where an observation image is to be generated using a desired wavelength set that is set by the wavelength set setting unit, an image is taken using illumination light corresponding to the emission light quantity ratio that is set by the light quantity ratio varying unit and is employed as an observation image if a wavelength range of a spectrum determined by the thus-set emission light quantity ratio overlaps with a wavelength range of the desired wavelength set, and, if overlap is not found, the light quantity ratio varying unit causes the white illumination light source to emit white light and the estimated spectral image generating unit generates an estimated spectral image corresponding to the desired wavelength set which is employed as an observation image.

According to this endoscope apparatus, even if the ratio of the light quantity of the special light source (405 nm) to that of the white illumination light source (445 nm) is set at 100:0, an observation image which includes a white light component can be generated through spectral estimation.

(10) In the endoscope apparatus of (9), the estimated spectral image generating unit generates an estimated spectral image from an image taken by lighting both of the white illumination light source and the special light source.

According to this endoscope apparatus, the amount of information of an estimated spectral image can be increased by necessarily leaving a wavelength component of the special light source (405 nm).

What is claimed is:

1. An endoscope apparatus, comprising:
an illuminating unit comprising plural light sources which generate light beams having different spectra, which illuminates an observation subject;
an imaging unit which images the observation subject;
an observation magnification varying unit which varies observation magnification of the imaging of the imaging unit;
a light quantity ratio varying unit which continuously varies an emission light quantity ratio between the plural light sources according to the observation magnification that is set by the observation magnification varying unit,
wherein the illuminating unit comprises a white illumination light source and a special light source for generating different illumination light than the white illumination light source,
wherein the white illumination light source includes a semiconductor light-emitting device, and the special light source includes a semiconductor light-emitting device for generating light having such a center wavelength that a fine blood vessel structure in a surface layer of a living body tissue as the observation subject is emphasized, and
wherein the light quantity ratio varying unit increases a ratio of an emission light quantity of the special light source to an emission light quantity of the white illumination light source as the observation magnification increases, so as to emphasize the fine blood vessel structure as a degree of short-range-view observation becomes higher and so as to continuously vary the ratio according to a variation of the observation magnification;

a wavelength set setting unit which sets a wavelength set which includes a combination of plural wavelength ranges; and an estimated spectral image generating unit which generates an estimated spectral image which would be obtained when the observation subject is illuminated with light including a spectrum that is produced by the wavelength set that is set by the wavelength set setting unit by performing a matrix operation on an observation image taken by illuminating the observation subject with white illumination light, wherein, where an observation image is to be generated using a desired wavelength set that is set by the wavelength set setting unit, an image is taken using illumination light corresponding to the emission light quantity ratio that is set by the light quantity ratio varying unit and is employed as an observation image if a wavelength range of a spectrum determined by the emission light quantity ratio that is set overlaps with a wavelength range of the desired wavelength set, and, if an overlap is not found, the light quantity ratio varying unit causes the white illumination light source to emit white light and the estimated spectral image generating unit generates an estimated spectral image corresponding to the desired wavelength set which is employed as an observation image.

2. The endoscope apparatus according to claim 1, wherein the special light source includes a center wavelength that is in a range of 370 nm to 470 nm.

3. The endoscope apparatus according to claim 1, wherein the white illumination light source comprises the semiconductor light-emitting device and a wavelength conversion member including a phosphor which is excited at an emission wavelength of the semiconductor light-emitting device.

4. The endoscope apparatus according to claim 1, wherein the white illumination light source comprises semiconductor light-emitting devices for emitting red light, green light, and blue light, respectively.

5. The endoscope apparatus according to claim 1, wherein the observation magnification comprises a magnification of a variable magnification optical system.

6. The endoscope apparatus according to claim 1, wherein the observation magnification comprises a magnification of digital zoom processing.

7. The endoscope apparatus according to claim 1, wherein the estimated spectral image generating unit generates an estimated spectral image from an image taken by lighting both of the white illumination light source and the special light source.

8. An endoscope apparatus, comprising:

an illuminating unit comprising plural light sources which generate light beams having different spectra, which illuminates an observation subject;

an imaging unit which images the observation subject;

an observation magnification varying unit which varies observation magnification of the imaging of the imaging unit;

a light quantity ratio varying unit which continuously varies an emission light quantity ratio between the plural light sources according to the observation magnification that is set by the observation magnification varying unit, wherein the illuminating unit comprises a white illumination light source and a special light source for generating different illumination light than the white illumination light source, wherein the white illumination light source includes a semiconductor light-emitting device, and the special light source includes a semiconductor light-emitting device for generating light having such a center-wavelength that a fine blood vessel structure in a surface layer of a living body tissue as the observation subject is emphasized, and wherein the light quantity ratio varying unit increase& a ratio of an emission light quantity of the special light source to an emission light quantity of the white illumination light source as the observation magnification increases, so as to-emphasize the fine blood vessel structure as a degree of short-range-view observation becomes higher and so as to continuously vary the ratio according to a variation of the observation magnification;

a wavelength set setting unit which sets a wavelength set which includes a combination of plural wavelength ranges; and an estimated spectral image generating unit which generates-an estimated spectral image which would be obtained when the observation subject is illuminated with light including a spectrum that is produced by the wavelength set that is set by the wavelength set setting unit by performing a matrix operation on an observation image taken by illuminating the observation subject with white illumination light, wherein, where an observation image is to be generated using a desired wavelength set that is set by the wavelength set setting unit, an image is taken using illumination light corresponding to the emission light quantity ratio that is set by the light quantity ratio varying unit and is employed as an observation image, if a wavelength range of a spectrum determined by the emission light quantity ratio that is set overlaps with a wavelength range of the desired wavelength set, and, if the wavelength range of the spectrum determined by the emission light quantity ratio that is set does not overlap with a wavelength range of the desired wavelength set, the light quantity ratio varying unit causes the white illumination light source of the illuminating unit to emit white light and the estimated spectral image generating unit generates an estimated spectral image corresponding to the desired wavelength set which is employed as an observation image.

9. An endoscope apparatus, comprising:

an illuminating unit comprising plural light sources which generate light beams having different spectra, which illuminates an observation subject;

an imaging unit which images the observation subject;

an observation magnification varying unit which varies observation magnification of the imaging of the imaging unit;

a light quantity ratio varying unit which continuously varies an emission light quantity ratio between the plural light sources according to the observation magnification that is set by the observation magnification varying unit, wherein the illuminating unit comprises a white illumination light source and a special light source for generating different illumination light than the white illumination light source, wherein the white illumination light source includes a semiconductor light-emitting device, and the special light source includes a semiconductor light-emitting device for generating light having such a center wavelength that a fine blood vessel structure in a surface layer of a living body tissue as the observation subject is emphasized, and wherein the light quantity ratio varying unit increases a ratio of an emission light quantity of the special light source to an emission light quantity of the white illumination light source as the observation magnification increases, so as to emphasize the fine blood vessel structure as a degree of short-range-view observation becomes higher and so as to continuously vary the ratio according to a variation of the observation magnification;

a wavelength set setting unit which sets a wavelength set which includes a combination of plural wavelength ranges; and an estimated spectral image generating unit which generates an estimated spectral image which would be obtained when the observation subject is illuminated with light including a spectrum that is produced by the wavelength set that is set by the wavelength set setting unit by performing a matrix operation on an observation image taken by illuminating the observation subject with white illumination light, wherein, where an observation image is to be generated using a desired wavelength set that is set by the wavelength set setting unit, an image is taken using illumination light corresponding to the emission light quantity ratio that is set by the light quantity ratio varying unit and is employed as an observation image, if a wavelength range of a spectrum determined by the emission light quantity ratio that is set overlaps with a wavelength range of the desired wavelength set.

10. The endoscope apparatus according to claim 9, wherein, if the wavelength range of the spectrum determined by the emission light quantity ratio that is set does not overlap with a wavelength range of the desired wavelength set, the light quantity ratio varying unit causes the white illumination light source of the illuminating unit to emit white light and the estimated spectral image generating unit generates an estimated spectral image corresponding to the desired wavelength set.

11. An endoscope apparatus, comprising:

an illuminating unit comprising plural light sources which generate light beams having different spectra, which illuminates an observation subject;

an imaging unit which images the observation subject;

an observation magnification varying unit which varies observation magnification of the imaging of the imaging unit;

a light quantity ratio varying unit which continuously varies an emission light quantity ratio between the plural light sources according to the observation magnification that is set by the observation magnification varying unit, wherein the illuminating unit comprises a white illumination light source and a special light source for generating different illumination light than the white illumination light source, wherein the white illumination light source includes a-semiconductor light-emitting device, and the special light source includes a semiconductor light-emitting device for generating light having such a center wavelength that a fine blood vessel structure in a surface layer of a living body tissue as the observation subject is emphasized, and wherein the light quantity ratio varying unit increases a ratio of an emission light quantity of the special light source to an emission light quantity of the white illumination light source as the observation magnification increases, so as to emphasize the fine blood vessel-structure as a degree of short-range-view observation becomes higher and so as to continuously vary the ratio according to a variation of the observation magnification;

a wavelength set setting unit which sets a wavelength set which includes a combination of plural wavelength ranges; and an estimated spectral image generating unit which generates an estimated spectral image which would be obtained when the observation subject is illuminated with light including a spectrum that is produced by the wavelength set that is -set by the wavelength set setting unit, wherein, where an observation image is to be generated using a desired wavelength set that is set by the wavelength set setting unit, an image is taken using illumination light corresponding to the emission light quantity ratio that is set by the light quantity ratio varying unit and is employed as an observation image if a wavelength range of a spectrum determined by the emission light quantity ratio that is set overlaps with a wavelength range of the desired wavelength set.

12. The endoscope apparatus according to claim 11, wherein, if an overlap is not found, the light quantity ratio varying unit causes the white illumination light source to emit white light and the estimated spectral image generating unit generates an estimated spectral image corresponding to the desired wavelength set which is employed as an observation image.

* * * * *